United States Patent [19]

Ito et al.

[11] Patent Number: 5,476,979
[45] Date of Patent: * Dec. 19, 1995

[54] PROCESSES FOR CONVERTING CHLORINATED ALKENES TO USEFUL, LESS CHLORINATED ALKENES

[75] Inventors: Larry N. Ito; Craig B. Murchison, both of Midland, Mich.; Michael T. Holbrook, Baton Rouge, La.; A. Dale Harley, Baton Rouge, La.; David D. Smith, Baton Rouge, La.

[73] Assignee: The Dow Chemical Company, Midland, Mich.

[*] Notice: The portion of the term of this patent subsequent to Sep. 26, 2012, has been disclaimed.

[21] Appl. No.: 227,806

[22] Filed: Apr. 14, 1994

Related U.S. Application Data

[63] Continuation-in-part of Ser. No. 112,042, Aug. 26, 1993, abandoned, which is a continuation-in-part of Ser. No. 955,173, Oct. 1, 1992, abandoned.

[51] Int. Cl.$^6$ .............................. C07C 1/26; C07C 21/04
[52] U.S. Cl. .................... 585/641; 585/642; 570/216; 570/230
[58] Field of Search ...................... 585/641, 642, 585/733

[56] References Cited

U.S. PATENT DOCUMENTS

| 3,892,818 | 7/1975 | Schaufe | 423/481 |
| 4,895,995 | 1/1990 | James, Jr. et al. | 585/469 |
| 4,899,001 | 2/1990 | Kalnes | 585/310 |

FOREIGN PATENT DOCUMENTS

| 5-320076 | 12/1993 | Japan . |
| 94/22792 | 10/1994 | WIPO . |

Primary Examiner—P. Achutamurthy

[57] ABSTRACT

A process for converting a chlorinated alkene feedstock including two or more chlorines to reaction products including a less-chlorinated alkene in a commercially substantial proportion, comprising reacting the chlorinated alkene feedstock with hydrogen in the presence of a catalyst consisting essentially of a Group VIII metal other than rhodium, palladium or ruthenium and a Group IB metal on a support.

21 Claims, No Drawings

PROCESSES FOR CONVERTING CHLORINATED ALKENES TO USEFUL, LESS CHLORINATED ALKENES

This application is a continuation-in-part of U.S. patent application Ser. No. 08/112,042, filed Aug. 26, 1993, now abandoned, which is a continuation-in-part of U.S. patent application Ser. No. 07/955,173, filed Oct. 1, 1992, now abandoned.

The present invention relates generally to processes for converting chlorinated hydrocarbons to less chlorinated products and to the catalysts used in such processes.

European Patent Application EP 0496446A describes the preparation of chlorotrifluoroethylene and trifluoroethylene from 1,1,2-trichloro-1,2,2-trifluoroethane via a catalyst comprised of copper and a Group VIII metal (palladium and platinum being preferred) on a carbon support. Several prior publications address the same conversion and describe the same or different catalysts, see, for example EP 0253410B, EP 0355907B and EP 0459463A. None of these publications describes or suggests, however, that other halogenated feedstocks might be suitably catalytically converted to less halogenated and more useful or more salable materials, and in particular none of these references suggest that the catalysts described therein might be useful outside of the fluorocarbon art.

A seemingly separate course of development has occurred with respect to the class of chlorinated hydrocarbon feedstocks which are exclusive of the chlorofluorocarbon feedstocks, and within the art pertaining to this class of materials are a number of references which relate more particularly to the conversion of a chlorinated alkene feedstock (which hereafter shall be taken as excluding the chlorofluorocarbon materials) to a less chlorinated alkene product.

Canadian Patent No. 1,119,203, for example, describes the conversion of perchloroethylene to trichloroethylene via a catalyst including an activated carbon carrier, copper metal or a copper compound, one or more of the palladium, ruthenium or rhodium metals or compounds thereof, and optionally, an alkali metal compound as a promoter. Earlier processes for converting perchloroethylene to trichloroethylene in the presence of copper salts on alumina, and including activation by alkali metal salts are also described.

German Patent Publication DE 3804265A is similar to the Canadian reference in describing a method for preparing trichloroethylene from hydrogen and perchloroethylene over a carrier catalyst of an activated charcoal carrier, copper in an elemental or chemically-bonded (compound) form, rhodium in an elemental or chemically-bonded form, and an organic phosphine or phosphite promoter.

An earlier provisional specification is referenced in this publication which purportedly describes a method for preparing trichloroethylene from hydrogen and perchloroethylene, in which the catalyst uses an activated charcoal carrier, copper metal or a copper compound, and elemental palladium, ruthenium or rhodium or a compound thereof.

More recently, U.S. Pat. No. 5,091,603 to the same assignee describes a process for converting perchloroethylene to trichloroethylene via a catalyst including copper, rhodium or palladium, and a phosphonium halide promoter on activated carbon.

The present invention is similarly directed to processes for the catalytic conversion of a chlorinated alkene feedstock including two or more chlorines to reaction products including a desired, less-chlorinated alkene in a commercially-substantial proportion (that is, at a yield (defined as the selectivity to such corresponding, less-chlorinated alkene multiplied by the conversion, on an hydrogen chloride- and hydrogen-free basis) of at least about 10 percent, but more preferably at least about 20 percent and most preferably at least about 30 percent).

"Less chlorinated" it should be noted, embraces still-chlorinated hydrocarbons as well as hydrocarbons having no remaining chlorine atoms associated therewith. A particularly preferred application, however, is for the conversion of perchloroethylene to reaction products including trichloroethylene in a commercially-substantial proportion.

By a process of the present invention in a first, broad aspect, a selected chlorinated alkene feedstock including two or more chlorines is reacted with hydrogen in the presence of a supported catalyst which consists essentially of a Group VIII metal in an elemental or compound form which is other than rhodium, palladium or ruthenium (the Group VIII designation here and elsewhere deriving from the Periodic Table of the Elements, as published by Sargent-Welch Scientific Company, Skokie, Illinois USA as Catalog No. S-18806 (1979)), and a Group IB metal in elemental or compound form on a support.

In a related more preferred embodiment, however, the chlorinated alkene feedstock is converted to reaction products including a desired, less-chlorinated alkene in a commercially substantial proportion via a supported catalyst consisting essentially of (and preferably consisting entirely of) a Group VIII metal which is other than rhodium, palladium or ruthenium, a Group IB metal, and a promoter material. Again, an especially preferred application is for the production or trichloroethylene from perchloroethylene.

The desired product(s) of the contemplated processes are then conventionally separated from those which are not desired, and may be further processed in a conventional, known manner to be placed in condition for an appropriate use or for sale.

It is expected that the triarylphosphines and triarylphosphites mentioned in DE 3,804,265 can be suitable promoter materials for the catalyst according to this more preferred embodiment, as well as the water-soluble phosphonium halides mentioned in the above-cited U.S. Pat. No. 5,091,603, wherein unsubstituted, alkyl- and aryl-substituted triphenylphosphonium halides are specifically mentioned and preferred. A tetraphenyl tin promoter is exemplified below and also may be used, but at least with respect to the conversion of perchloroethylene to trichloroethylene, more preferably phosphorus is incorporated into the present catalysts as a promoter via impregnation of the support with an aqueous solution of a phosphonium halide (preferably) or via impregnation with an organic phosphine solution.

The support in these catalysts (and catalysts here includes those without and with a promoter material added) can be any of the known conventional inert supports, but is preferably silica or carbon, with carbon being most preferred. The carbon is preferably a high surface area carbon, for example, a carbon having a specific surface area in an unimpregnated condition of about 200 $m^2/g$ or more, especially about 400 $m^2/g$ or more, and most especially about 600 $m^2/g$ or more.

An example of a commercially-available carbon which has been found to be useful in the present invention is a coal-based carbon produced by Calgon Carbon Corporation under the designation "BPLF3", and may generally be characterized as having a specific surface area of 1100 $m^2/g$ to 1300 $m^2/g$, a pore volume of 0.7 to 0.85 $cm^3/g$, and an average pore radius of 12.3 to 14 angstroms. Other carbons may be employed, for example, a coconut-based carbon such as produced by Calgon Carbon Corporation under the designation PCB (having a published specific surface area of from 1150 to 1250 m²/g and a pore volume of 0.72 cm³/g) or a wood-based carbon such as produced by Calgon Carbon Corp. as WSIV Special carbon (having a published or reported specific surface area of 1400 m²/g, and a pore volume of 1.25 cm³/g).

The appropriate proportions and amounts of the Group VIII metal and Group IB metal, and Group VIII metal, Group IB metal and phosphorus or other selected promoter in the more preferred catalysts can vary depending on the circumstances of the catalyst's intended use and on the method of catalyst preparation which is employed. In general terms, however, and for a catalyst prepared by solution impregnation (including more particularly coimpregnation) of the carrier, the selected Group IB metal (preferably copper) can be anywhere from about 0.01 to about 30 percent by weight on an elemental basis of the catalyst, with a selected Group VIII metal (preferably platinum) comprising from about 0.01 to about 5.0 percent by weight on an elemental basis of the catalyst and the promoter (where employed) comprising from about 0.01 to about 10 percent by weight of the catalyst.

The reaction conditions can also vary, depending for example on the particular catalyst and the particular chlorinated alkene feedstock involved, or more particularly depending on whether the process is to be conducted in the gas phase or liquid phase.

In general, in the gas phase processes reaction pressures can range from atmospheric up to about 1500 psig, with temperatures of from about 100 deg. C. to about 350 deg. C., residence times of from about 0.25 seconds to about 180 seconds, and hydrogen/chlorinated alkene feed ratios ranging on a molar basis from about 0.1:1 to about 100:1.

More preferably, reaction pressures will range from about 5 psig to about 500 psig, with temperatures of from about 140 deg. C. to about 300 deg. C., residence times of from about 0.5 seconds to about 120 seconds, and hydrogen/chlorinated alkene feed ratios of from about 0.3:1 to about 20:1.

Most preferably, reaction pressures in the gas phase processes will range from about 40 psig to about 300 psig, with temperatures of from about 160 deg. C. to about 260 deg. C., residence times of from about 1 second to about 90 seconds, and hydrogen/chlorinated alkene molar feed ratios of from about 0.50:1 to about 6:1.

In the liquid phase processes (which can be conducted in a batchwise or continuous manner, as desired), it is anticipated that the reaction pressures will generally range from atmospheric up to about 3000 psig, at temperatures of from about 25 degrees Celsius to about 350 degrees Celsius, residence times of from about 1 to about 30 minutes and hydrogen to chlorinated alkene molar feed ratios of from about 0.1:1 to about 100:1.

A most preferred application and use of the present invention, as has already been mentioned previously, is in the development of an improved, gas phase process for the conversion of perchloroethylene to reaction products including trichloroethylene in a commercially substantial proportion.

According to this improved process, perchloroethylene is reacted with hydrogen in the presence of a supported catalyst consisting essentially of a Group VIII metal (other than rhodium, palladium and ruthenium) in elemental or compound form, a Group IB metal in elemental or compound form, and a phosphorus promoter, for example, from an impregnation of the support with an aqueous solution of methyltricyclohexylphosphonium chloride or with an organic solution of tricyclohexylphosphine, with impregnation with the methyltricyclohexylphosphonium chloride being preferred. A preferred catalyst for this perchloroethylene to trichloroethylene process will consist entirely of the Group VIII metal, Group IB metal and prescribed phosphorus promoter on a support.

In this regard, it has been found by the present invention that bimetallic catalysts for converting perchloroethylene to trichloroethylene can be made from a Group IB metal such as copper and the Group VIII metals other than rhodium, palladium or ruthenium, which under the same conditions can be as or more effective in such conversion as the known, phosphonium halide-promoted rhodium catalysts described in U.S. Pat. No. 5,091,603. Still more effective catalysts can be prepared by the addition of a promoter (especially, but not limited to, a phosphorus promoter), whereby significant differences in performance may be seen between a comparable rhodium-based catalyst as described in the '603 patent and a platinum-based catalyst of the present invention.

A most preferred catalyst for use in the improved perchloroethylene to trichloroethylene process contemplated herein, will thus consist of platinum (as the Group VIII metal), copper (as the Group IB metal) and phosphorus (from an aqueous solution of methyltricyclohexylphosphonium chloride or from a solution of tricyclohexylphosphine in an organic solvent) on a support, which support is preferably a high surface area carbon of a type described above.

In more particular terms, this most preferred catalyst preferably contains from about 0.01 to about 5.0 percent by weight of platinum (calculated on an elemental basis), from about 0.5 to about 30 percent by weight of copper (also calculated on an elemental basis) and from about 0.01 to about 10 percent by weight of phosphorus from an aqueous solution of methyltricyclohexylphosphonium chloride (preferably) or from an organic solution of tricyclohexylphosphine, on a carbon support having a specific surface area of at least about 200 m²/g.

More preferably, the catalyst includes from about 0.02 to about 3.0 percent by weight of platinum, from about 1 to about 20 percent by weight of copper and from about 0.02 to about 7.5 percent by weight on an elemental basis of phosphorus from one of these solutions, and the carbon support has a specific surface area of at least about 500 m²/g.

Most preferably, the catalyst includes from about 0.04 to about 1.0 percent by weight of platinum, from about 4 to about 15 percent by weight of copper and from about 0.03 to about 5.0 percent by weight of phosphorus from one of the solutions, and the carbon support has a specific surface area of at least about 800 m²/g. A presently preferred carbon is the wood-based WSIV Special activated carbon (Calgon Carbon Corporation) having a published specific surface area of about 1400 m²/g.

The pressure under which this reaction is conducted preferably ranges from atmospheric pressure to about 1500 psig, more preferably from about 15 psig to about 500 psig, and most preferably from about 30 psig to about 300 psig. The temperature will preferably be from about 100 deg. C. to about 350 deg. C., more preferably will be from about 140 deg. C. to about 280 deg. C., and most preferably will be from about 160 deg. C. to about 250 deg. C. Preferred residence times will be from about 0.25 seconds to about 180 seconds, more preferably will be from about 20 seconds to about 120 seconds, and most preferably will be from about 30 seconds to about 100 seconds. Hydrogen to perchloroethylene molar feed ratios will preferably be from about 0.1:1 to about 100:1. More preferably, the hydrogen to perchloroethylene feed ratios will be from about 0.3:1 to about 10:1, and most preferably from about 0.5:1 to about 3.0:1.

While the preceding discussion has focused specifically on the conversion of chlorinated alkenes to desired, less chlorinated alkenes, those skilled in the art will also recognize that the processes of the present invention may be combined with other, perhaps conventional processes if expedient for the handling and disposition of various chlorinated feedstocks, and particularly for the expedient processing of streams including other chlorinated byproducts in addition to chlorinated alkene byproducts.

ILLUSTRATIVE EXAMPLES

The present invention is more particularly illustrated by the examples which follow hereafter.

Examples 1–3: Experimental Apparatus and Procedure

Examples 1–3 focus on the gaseous phase reaction, over several catalysts, of hydrogen and perchloroethylene to produce reaction products including trichloroethylene.

Perchloroethylene was pumped for these examples via a piston pump through 1/16th inch (1.6 mm) (O.D.) nickel tubing to a Monel™ alloy (Huntington Alloys, Inco Alloys International, Inc.) gas sample cylinder packed with glass beads (unless specifically noted, all fittings and tubing were of Monel™ alloy), at a liquid hourly space velocity (LHSV) of 0.075 (where LHSV= volume liquid perchloroethylene fed per hour per packed bed volume of catalyst in the subsequent reactor). The 1/16th inch tubing extended to the center of the sample cylinder, with the sample cylinder being heated to a vaporization temperature of 110 degrees Celsius by electrical heat tracing. A thermocouple was used to monitor the skin temperature of the sample cylinder.

The flow of the hydrogen feed stream was controlled by a pre-calibrated mass flow controller, at a molar feed ratio of 1.5 to 1 of hydrogen to perchloroethylene. The hydrogen was passed through the heated sample cylinder, where mixing of the gaseous perchloroethylene and hydrogen occurred. The mixed gases were then passed into a charged Monel™ tubular reactor (0.50 in. (1.27 cm) O.D., 21 inches (53.3 cm.) in length) heated by ceramic lined electric elements to a desired reaction temperature, and reacted over a residence time of 47.7 seconds.

The catalyst (20.0 cubic centimeters) was in each case charged into the reactor between 3 mm glass beads, and placed in the middle of the reactor. The catalyst was thereafter dried under a flow of nitrogen for one hour at 130 degrees Celsius, and then reduced the catalyst under a 5:1 molar ratio of flowing nitrogen and hydrogen. In reducing the catalyst, the temperature was ramped up from 130 to 220 degrees Celsius at 3 degrees per minute, and then held at 220 degrees for a total reducing cycle time of about 2 hours.

Upon reaction of the mixed hydrogen and perchloroethylene in the reactor at the prescribed reaction temperature, the effluent from the reactor passed to a gas sampling valve, which provided gaseous aliquots for online gas chromatographic analysis in a Hewlett-Packard Model 5790 gas chromatograph (Hewlett-Packard Company). The gas chromatograph was equipped with a thermal conductivity detector, and used a 30 meter by 0.53 millimeter (I.D.), 5 percent phenyl, 95 percent methyl silicone/fused silica column to separate the various reaction products. Response factors were conventionally determined by injections of gravimetrically-prepared standards of the individual reaction products. These response factors were applied in conjunction with individual peak areas and the total mols of all reaction products to determine the mol percents of individual components in the reactor effluent, and the selectivity to individual reaction products as described above. Catalyst productivity (in kg/m$^3$.hr) was additionally calculated by dividing the number of kilograms of trichloroethylene produced per hour by the cubic meters of catalyst used to produce the trichloroethylene.

EXAMPLE 1

For this example, a catalyst was prepared which consisted of 0.1 percent by weight (on an elemental basis) of platinum, 10 percent by weight of copper and 0.37 percent by weight of tin on a carbon support, and was compared to a catalyst consisting of 0.1 percent by weight on an elemental basis of platinum and 10 percent by weight of copper on the same carbon support, and to a catalyst consisting of 0.1 percent by weight of tin and 10 percent by weight of copper on the carbon support.

The platinum/copper catalyst was prepared by first dissolving 12.732 grams of CuCl$_2$ (Aldrich Chemical Co., Inc., Catalog No. 22-201-1, 97 percent purity, containing approximately 0.46 percent of sodium, 0.13 percent of zinc, 380 parts per million of iron, 120 parts per million of sulfur, 120 parts per million of phosphorus and 500 parts per million of calcium as impurities) in 80.00 mL of distilled and deionized water. 60.15 grams of Calgon's WSIV Special activated carbon having a published specific surface area of 1400 m$^2$/g were added to the CuCl$_2$ solution, and the flask was agitated rapidly to evenly coat the carbon carrier with the CuCl$_2$ solution. The impregnated carrier was then dried in an evaporating dish in air at ambient temperatures for 18 hours. Thereafter, the carbon carrier was further air-dried in an oven at 120 degrees Celsius for 2 hours.

An aqueous H$_2$PtCl$_6$ stock solution was then prepared by dissolving 1.342 grams of H$_2$PtCl$_6$·XH$_2$O (J. T. Baker, Inc., Baker Analyzed Grade, 37.5 percent platinum) in 50.00 mL of distilled, deionized water. 1.000 grams of this solution were placed in a 50 mL Erlenmeyer flask and diluted with 7.00 grams of distilled, deionized water. 9.98 grams of the dried, copper-impregnated carbon carrier were then added to the flask, and the flask agitated to evenly coat the carbon with the aqueous H$_2$PtCl$_6$ stock solution. The resulting catalyst was then dried in an evaporating dish in air at ambient temperatures for 18 hours, and further dried in an oven in air at 120 degrees Celsius for 2 hours.

The tin/copper catalyst was prepared for comparison by dissolving 0.0329 grams of Sn(C$_6$H$_5$)$_4$ (Aldrich Chemical Co., Inc.) in 20.00 grams of perchloroethylene in a 50 mL Erlenmeyer flask. 9.14 grams of the previously-dried, copper-impregnated carbon material were then added to the flask with swirling to evenly coat the carbon with the Sn(C$_6$H$_5$)$_4$ solution. The catalyst was air-dried, again, in an evaporating dish for 18 hours at ambient temperatures, and then dried for 2 hours at 120 degrees Celsius.

The platinum/tin/copper catalyst was prepared by dissolving 0.122 grams of Sn(C$_6$H$_5$)$_4$ in 48.69 grams of perchloroethylene in a 125 mL Erlenmeyer flask. 17.23 grams of the previously-dried platinum/copper catalyst were added to the flask with swirling to coat the solution onto the carbon support, and the resulting catalyst was air-dried at ambient temperatures for 18 hours, then at 120 degrees Celsius for 2 hours.

Single charges of each of these catalysts were dried, reduced and evaluated at several temperatures with the apparatus and according to the procedures described above, with the results shown in Table 1.

TABLE 1

| Catalyst | T (°C.) | Conversion (%) | Selectivity (%) | | | | Productivity (kg/m$^3$ · hr) |
|---|---|---|---|---|---|---|---|
| | | | TCE[a] | trans- $C_2H_2Cl_2$ | cis- $C_2H_2Cl_2$ | Other | |
| 0.1 Pt/0.37 Sn/10 Cu//C | 187 | 33.02 | >99 | — | — | — | 30.4 |
| | 200 | 73.71 | 95.5 | 1.6 | 2.9 | — | 65.6 |
| | 210 | 87.20 | 93.9 | 1.9 | 4.2 | — | 76.8 |
| | 215 | 90.26 | 92.2 | 2.4 | 4.6 | 0.7[b] | 78.4 |
| 0.1 Pt/10 Cu//C | 190 | 23.47 | >99 | — | — | — | 22.4 |
| | 200 | 33.08 | 98.8 | 1.2 | — | — | 30.4 |
| | 210 | 50.68 | 96.0 | 2.2 | 1.8 | — | 46.4 |
| | 220 | 80.12 | 92.7 | 3.4 | 3.9 | — | 70.4 |
| 0.1 Sn/10 Cu//C | 200 | 5.6 | >99 | — | — | — | 4.8 |
| | 210 | 8.1 | >99 | — | — | — | 8.0 |

[a] = TCE = trichloroethylene
[b] = Vinyl Chloride

EXAMPLE 2

A platinum/tin/copper catalyst was prepared, charged, reduced and tested in this example which contained 0.044 percent by weight of platinum, 0.023 percent by weight of tin, and 10.0 percent by weight of copper.

An aqueous $H_2PtCl_6$ stock solution was prepared by dissolving 2.684 grams of $H_2PtCl_6 \cdot XH_2O$ (37.5% Pt, J. T. Baker, Inc., Baker Analyzed Grade) in 100.00 mL of distilled, deionized water. 2.122 grams of the stock solution and 10.138 grams of the 97% purity $CuCl_2$ Aldrich salt were placed in a 250 mL Erlenmeyer flask, and diluted with swirling with 52.00 grams of distilled water. 38.27 grams of Calgon's WSIV Special activated carbon were added to the flask with rapid agitation. The catalyst was dried in an evaporating dish in air at ambient temperatures for 18 hours, after which the catalyst was further air-dried in an oven at 120 degrees Celsius for 2 hours. A solution of $Sn(C_6H_5)_4$ dissolved in $C_2Cl_4$ was prepared by dissolving 0.0352 grams of this salt in 40.00 grams of $C_2Cl_4$ in a 250 mL Erlenmeyer flask. 42.69 grams of the previously dried catalyst was added to this flask with rapid agitation. The catalyst was again air-dried at ambient temperatures for 18 hours, and then in an oven at 120 degrees Celsius for 2 additional hours.

The results of the evaluation are as shown below in Table 2.

EXAMPLE 3

A platinum/tin/copper catalyst was also prepared in this example, but a $CuCl_2$ salt of 99.999 percent purity was used to start rather than a 97 percent purity salt as in Example 2. In addition, the relative amount of tin was increased substantially, from 0.023 percent by weight in the previous example, to 0.15 percent by weight on an elemental basis.

The results of testing on a charge of this catalyst at various temperatures are provided in Table 3, all other circumstances and conditions being the same as in the immediately preceding examples:

TABLE 2

| Catalyst | T (°C.) | Conversion (%) | Selectivity (%) | | | Productivity (kg/m$^3$ · hr) |
|---|---|---|---|---|---|---|
| | | | TCE[a] | trans- $C_2H_2Cl_2$ | cis- $C_2H_2Cl_2$ | |
| 0.044 Pt/0.023 Sn/10 Cu//C | 190 | 12.68 | >99 | — | — | 11.2 |
| | 200 | 22.54 | >99 | — | — | 20.8 |
| | 210 | 38.89 | 95.3 | 3.0 | 1.7 | 35.2 |
| | 220 | 65.86 | 92.5 | 4.6 | 2.8 | 57.6 |

[a] = TCE = trichloroethylene

TABLE 3

| Catalyst | T (°C.) | Conversion (%) | Selectivity (%) | | | Productivity (kg/m³ · hr) |
|---|---|---|---|---|---|---|
| | | | TCE[a] | trans-$C_2H_2Cl_2$ | cis-$C_2H_2Cl_2$ | |
| 0.044 Pt/0.15 Sn/10 Cu//C | 190 | 10.71 | >99 | — | — | 9.6 |
| | 200 | 15.68 | >99 | — | — | 14.4 |
| | 210 | 23.32 | >99 | — | — | 22.4 |
| | 220 | 32.15 | 94.5 | 5.5 | — | 28.8 |

[a] = TCE = trichloroethylene

EXAMPLE 4

In this example, 1,3-dichloropropene was dechlorinated over a supported platinum/copper catalyst of the present invention containing 0.25 percent by weight of platinum and 0.50 percent by weight of copper. This catalyst was prepared by dissolving $H_2PtCl_6 \cdot H_2O$ in water, adding a proportionate amount of $CuCl_2$ with swirling to dissolve the $CuCl_2$, and diluting with deionized, distilled water. Calgon BPLF3 activated carbon (6×16 mesh, Calgon Carbon Corp., Pittsburgh, Pa.) was then added to the flask containing the Pt/Cu solution, and the flask agitated rapidly so that the carbon carrier was evenly coated with the aqueous Pt/Cu solution. The catalyst preparation was dried in an evaporating dish in air at ambient temperatures for 18 hours, and then further dried in an oven in air at 120 degrees Celsius for 2 hours.

A 0.6 gram catalyst charge was thereafter placed in a tubular reactor described more particularly below, over a glass wool support contained in the center of the reactor tubing. The catalyst was then covered with a plug of glass wool.

The charged catalyst was dried in place for from 8 to 24 hours at 150 degrees Celsius under a nitrogen purge. The catalyst was thereafter reduced by passing hydrogen through the reactor at a flow rate of 34 mL/minute for 24 hours, and the reactor temperature was lowered to the desired temperature of 220 degrees Celsius. The reactor temperature and hydrogen gas flow (as metered in by an apparatus described below) were allowed to equilibrate for about 1 hour before the liquid feedstock flow was started into the apparatus.a.

In conducting the reaction, the 1,3-dichloropropene feedstock was then pumped via a high pressure syringe pump through 1.6 mm (O.D.) (1/16 inch) Monel™ nickel alloy tubing (unless specifically noted below all of the components, tubing and fittings of the test reactor apparatus were also made of Monel™ nickel alloy (Huntington Alloys, Inco Alloys International, Inc.)) into a packed sample cylinder serving as a feed evaporator.

The 1/16th inch tubing extended almost to the center of the packed cylinder, which was heated to a vaporizing temperature of 180 degrees Celsius using electrical heat tracing. Vaporization of the 1,3-dichloropropene was accomplished in the feed line, so that the 1,3-dichloropropene was superheated when combined with the hydrogen feed stream. Thermocouples were used to monitor the skin temperature of the feed evaporator and the temperature of the gas exiting the feed evaporator, and the temperature of the feed evaporator was controlled by computer.

The hydrogen feed stream was metered throughout to a preheater using a Model 8249 linear mass flow controller from Matheson Gas Products, Inc. Secaucus, N.J., with the preheater consisting of a packed sample cylinder wrapped with electrical heat tracing. Thermocouples were used to monitor both the skin temperature of the preheater and the temperature of the gas exiting the preheater. The preheater temperature was set and maintained at 140 degrees Celsius.

Vaporized 1,3-dichloropropene exiting the evaporator was mixed with the hydrogen gas from the preheater at a 10.0 to 1 molar ratio of hydrogen to 1,3-dichloropropene, in a 2 foot (0.61 meter) long section of ¼ inch (0.64 cm) tubing maintained at a temperature of 140 degrees Celsius. The mixed gases then were passed into and reacted within a tubular reactor (½ inch (1.27 cm) O.D., 12 inches (30.5 cm) in length) located within an aluminum block heated by a cartridge heater and regulated via a computer to maintain the reaction temperature of 220 degrees Celsius, over a residence time of 0.8 seconds.

After reacting the 1,3-dichloropropene and hydrogen in the vapor phase in the tubular reactor thus prepared, the products from the reaction were passed to a gas sampling valve, which provided gaseous aliquots for online gas chromatographic analysis in a Hewlett-Packard Model 5890 Series II gas chromatograph (Hewlett-Packard Company). The gas chromatograph was equipped with a flame ionization detector, and used 30 meter by 0.53 millimeter (I.D.) 100 percent methyl silicone/fused silica and 30 meter by 0.53 millimeter (I.D.) porous polymer-lined fused silica columns to separate the various reaction products. Response factors were conventionally determined by injections of gravimetrically-prepared standards of the individual reaction products. These response factors were applied in conjunction with individual peak areas and the total mols of all reaction products to determine the mol percents of individual components in the reactor effluent, and the selectivity to individual reaction products.

Under the conditions of this Example, 4 percent of the 1,3-dichloropropene was converted to reaction products including propylene (at 30 percent selectivity), allyl chloride (5 percent selectivity) and 1-chloropropene (20 percent selectivity) with the remainder being miscellaneous hydrocarbons.

EXAMPLE 5

The apparatus and procedures generally of Examples 1–3 were employed to convert perchloroethylene to trichloroethylene via a catalyst containing 0.1 percent by weight of platinum and 2.5 percent by weight of copper on an elemental basis, on a WSIV carbon support. The reaction pressure was set for this example at 40 psig, with a hydrogen to perchloroethylene molar feed ratio of 1.0:1, an average residence time of 20.5 seconds and a reaction temperature of 218 degrees Celsius. Under these particular conditions and with this catalyst, 39.4 percent of the perchloroethylene was initially converted to reaction products including trichloroethylene (at 96.0 percent selectivity), for a productivity of the catalyst to trichloroethylene in this example of 381 kilograms per cubic meter of catalyst per hour.

EXAMPLES 6 AND 7

Using again the apparatus and general procedures of Examples 1–3, catalysts were evaluated in these examples which respectively consisted of 0.05 weight percent of platinum and 2.5 weight percent of copper on a WSIV carbon support, and 0.06 percent by weight of iridium with 2.5 weight percent of copper on a WSIV carbon support. Charges of these catalysts were evaluated at a reaction pressure of 40 psig, a hydrogen to perchloroethylene molar feed ratio of 1.0:1, and an average residence time of 30 seconds, but at several reaction temperatures. The results of the runs with the two catalysts at these several reaction temperatures are shown in Table 4, wherein catalyst "A" is the platinum/copper catalyst and catalyst "B" is the iridium/copper catalyst:

TABLE 4

| Catalyst | Temp. | Pct. Conversion | Selectivity[a] | Productivity (kg/m$^3$ · hr) |
|---|---|---|---|---|
| A | 190 | 14.1 | 97.6 | 114 |
|   | 200 | 22.6 | 97.2 | 182 |
|   | 210 | 35.0 | 95.2 | 275 |
|   | 220 | 52.9 | 92.2 | 403 |
| B | 190 | 5.1  | 99.3 | 41.8 |
|   | 200 | 13.6 | 98.4 | 111 |
|   | 210 | 25.3 | 96.4 | 201 |

[a]To Trichloroethylene;

EXAMPLE 8

A promoted, WSIV carbon-supported catalyst was prepared in the manner of previous examples which contained 0.1 percent by weight of platinum, 10.0 percent of copper, and 0.14 percent by weight of phosphorus on an elemental basis by impregnation from an aqueous solution of methyltricyclohexylphosphonium chloride (corresponding to 1.5 percent by weight of the catalyst as a compound). This catalyst was evaluated in the manner of Examples 1–3 above at several reaction temperatures, at a reaction pressure of 60 psig, a hydrogen to perchloroethylene molar feed ratio of 0.70:1 and an average residence time of 46 seconds. The results are shown in Table 5 as follows:

TABLE 5

| Temp. | Pct. Conversion | Selectivity[a] | Productivity (kg/m$^3$ · hr) |
|---|---|---|---|
| 180 | 10.0 | 99.0 | 81.8 |
| 190 | 22.8 | 96.9 | 183 |
| 200 | 35.5 | 95.1 | 279 |
| 210 | 54.0 | 92.0 | 411 |

[a]To Trichloroethylene;

COMPARATIVE EXAMPLE 1

The results of the preceding Example 8 may be compared with the results of runs at the same reaction temperatures and same conditions, with a WSIV carbon-supported catalyst within the teachings of U.S. Pat. No. 5,091,603 to Dafinger et al. and employing rhodium, copper and phosphorus from the same phosphonium halide promoter as used in Example 8. The catalyst for this example accordingly consisted of 0.044 weight percent of rhodium, 10.0 weight percent of copper and 0.14 weight percent of phosphorus on an elemental basis on the WSIV carbon support, and the results of the evaluation of this catalyst are shown in Table 6:

TABLE 6

| Temp. | Pct. Conversion | Selectivity[a] | Productivity (kg/m$^3$ · hr) |
|---|---|---|---|
| 180 | 7.9  | 99.2 | 64.8 |
| 190 | 12.4 | 99.0 | 101 |
| 200 | 18.2 | 98.9 | 149 |
| 210 | 29.3 | 98.7 | 239 |

[a]To Trichloroethylene;

EXAMPLE 9

The catalyst system of Example 8 was essentially reproduced, except that 0.15 weight percent of phosphorus was placed on the support from an aqueous solution of methyltriphenylphosphonium chloride (corresponding to 1.5 weight percent for the methyltriphenylphosphonium chloride as a compound, methyltriphenylphosphonium chloride being specifically mentioned and exemplified as a preferred phosphonium halide promoter material in the '603 patent). This catalyst was evaluated under the same conditions and at the same temperatures as in Example 8, with the results shown in Table 7:

TABLE 7

| Temp. | Pct. Conversion | Selectivity[a] | Productivity (kg/m$^3$ · hr) |
|---|---|---|---|
| 180 | 9.5  | 98.4 | 77.2 |
| 190 | 17.6 | 98.0 | 143 |
| 200 | 31.4 | 96.0 | 249 |
| 210 | 51.4 | 92.6 | 393 |

[a]To Trichloroethylene;

COMPARATIVE EXAMPLE 2

For comparison to Example 9, a rhodium-based catalyst was prepared using the same methyltriphenylphosphonium chloride, to provide a catalyst consisting of 0.044 weight percent of rhodium, 10.0 weight percent of copper and 0.15 weight percent of phosphorus on an elemental basis on the WSIV carbon support. This catalyst preparation was evaluated under the same conditions as in Example 9, with the results shown in Table 8:

TABLE 8

| Temp. | Pct. Conversion | Selectivity[a] | Productivity (kg/m$^3$ · hr) |
|---|---|---|---|
| 180 | 7.4  | 99.4 | 60.8 |
| 190 | 13.0 | 98.7 | 106 |
| 200 | 16.4 | 98.8 | 134 |
| 210 | 27.0 | 98.5 | 220 |

[a]To Trichloroethylene;

What is claimed is:

1. A process for converting a chlorinated alkene feedstock including two or more chlorines to reaction products including a less chlorinated alkene, comprising reacting the chlorinated alkene feedstock with hydrogen in the presence of a catalyst consisting essentially of a Group VIII metal other than rhodium, palladium or ruthenium and a Group IB metal on a support, under conditions effective to produce the less chlorinated alkene in a yield of at least about 10 percent.

2. A process as defined in claim 1, wherein the catalyst consists of a Group VIII metal which is other than palladium, rhodium or ruthenium and a Group IB metal on a support.

3. A process as defined in claim 2, wherein the Group VIII metal is platinum and the Group IB metal is copper.

4. A process for converting a chlorinated alkene feedstock including two or more chlorines to reaction products including a less-chlorinated alkene, comprising reacting the chlorinated alkene feedstock with hydrogen in the presence of a catalyst consisting essentially of a Group VIII metal other than rhodium, palladium or ruthenium, a Group IB metal and a promoter on a support, under conditions effective to produce the less chlorinated alkene in a yield of at least about 10 percent.

5. A process as defined in claim 4, wherein the catalyst consists of a Group VIII metal which is other than palladium, rhodium or ruthenium, a Group IB metal and a promoter on a support.

6. A process as defined in claim 5, wherein the Group VIII metal is platinum, and the Group IB metal is copper.

7. A process as defined in claim 6, wherein the promoter is tin or phosphorus.

8. A process as defined in claim 7, wherein the promoter is phosphorus and is incorporated into the catalyst by impregnation from an aqueous solution of a phosphonium halide or from an organic phosphine solution.

9. A process as defined in claim 8, wherein the phosphorus is incorporated into the catalyst by impregnation from an aqueous solution of a phosphonium halide.

10. A process for converting perchloroethylene to reaction products including trichloroethylene, comprising reacting perchloroethylene with hydrogen in the presence of a catalyst consisting essentially of a Group VIII metal other than rhodium, palladium or ruthenium, a Group IB metal and a promoter on a support, under conditions effective to produce trichloroethylene in a yield of at least about 10 percent.

11. A process as defined in claim 10, wherein the catalyst consists of a Group VIII metal which is other than palladium, rhodium or ruthenium, a Group IB metal and a promoter on a support.

12. A process as defined in claim 11, wherein the Group VIII metal is platinum, and the Group IB metal is copper.

13. A process as defined in claim 12, wherein the promoter is tin or phosphorus.

14. A process as defined in claim 13, wherein the promoter is phosphorus and is incorporated into the catalyst by impregnation from an aqueous solution of a phosphonium halide or from an organic phosphine solution.

15. A process as defined in claim 14, wherein the phosphorus is incorporated into the catalyst by impregnation from an aqueous solution of a methyltricyclohexylphosphonium chloride or from an organic solution of tricyclohexylphosphine.

16. A process as defined in claim 10 or claim 14, wherein the support is a carbon support having a specific surface area in an unimpregnated condition of at least about 200 $m^2/g$.

17. A process as defined in claim 16, wherein the support is a carbon support having a specific surface area in an unimpregnated condition of at least about 400 $m^2/g$.

18. A process as defined in claim 16, wherein the support is a carbon support having a specific surface area in an unimpregnated condition of at least about 600 $m^2/g$.

19. A process for converting perchloroethylene to reaction products including trichloroethylene, comprising reacting perchloroethylene with hydrogen in the presence of a catalyst consisting of from about 0.01 to about 5.0 weight percent on an elemental basis of platinum, from about 0.5 to about 30 percent by weight of copper on an elemental basis, and from about 0.01 to about 10.0 weight percent on an elemental basis of a phosphorus promoter on a carbon support having a specific surface area in an unimpregnated condition of at least about 200 $m^2/g$, the phosphorus promoter having been incorporated in the catalyst by impregnation from an aqueous solution of methyltricyclohexylphosphonium chloride or from a solution of tricyclohexylphosphine in an organic solvent, under conditions effective to produce trichloroethylene in a yield of at least about 10 percent.

20. A process as defined in claim 19, wherein the catalyst consists of from about 0.02 to about 3.0 weight percent of platinum, from about 1 to about 20 percent by weight of copper and from about 0.02 to about 7.5 weight percent of phosphorus on a carbon support having a specific surface area in an unimpregnated condition of at least about 400 $m^2/g$.

21. A process as defined in claim 20, wherein the catalyst consists of from about 0.04 to about 1.0 weight percent of platinum, from about 4 to about 15 percent by weight of copper and from about 0.03 to about 5.0 weight percent of phosphorus on a carbon support having a specific surface area in an unimpregnated condition of at least about 600 $m^2/g$.

* * * * *